United States Patent [19]

Irick, Jr. et al.

[11] 3,957,813

[45] May 18, 1976

[54] BENZOXAZOLYL PHENYL AROMATIC ESTER COMPOUNDS AND THEIR USE AS ULTRAVIOLET STABILIZERS IN ORGANIC COMPOSITIONS

[75] Inventors: Gether Irick, Jr.; Charles A. Kelly, both of Kingsport, Tenn.

[73] Assignee: Eastman Kodak Company, Rochester, N.Y.

[22] Filed: July 10, 1974

[21] Appl. No.: 484,848

[52] U.S. Cl. .................... 260/307 D; 252/301.28; 252/301.27; 260/45.8 R; 260/45.8 A; 260/45.8 N; 260/45.8 NT; 260/45.8 SN; 260/45.8 NZ; 260/304 R; 260/308 B; 260/309.2; 260/326.13 R
[51] Int. Cl.$^2$ .................................... C07D 263/56
[58] Field of Search .............................. 260/307 D

[56] References Cited
UNITED STATES PATENTS 3,551,443  12/1970  Duennenberger et al. .......... 260/307

3,864,354  2/1975  Irick et al. ...................... 260/307 D

*Primary Examiner*—Raymond V. Rush
*Attorney, Agent, or Firm*—Clyde L. Tootle; Daniel B. Reece, III

[57] ABSTRACT

The invention relates to benzoxazolyl phenyl aromatic ester compounds which have been found to be effective ultraviolet stabilizers. The invention also relates to ultraviolet degradable organic compositions containing an amount of a heterocyclic benzoate composition to prevent such degradation. These stabilizers are effective in the presence of other additives commonly employed in polymeric compositions including, for example, pigments, colorants, fillers, reinforcing agents and the like. These ultraviolet stabilizers may be incorporated into the organic compositions such as polymers by adding to the polymer melt or dissolved in the polymer dope, coated on the exterior of the shaped or molded article, film or extruded fiber.

16 Claims, No Drawings

BENZOXAZOLYL PHENYL AROMATIC ESTER COMPOUNDS AND THEIR USE AS ULTRAVIOLET STABILIZERS IN ORGANIC COMPOSITIONS

This invention relates to heterocyclic benzoate ultraviolet stabilizers and their use in organic compositions. More particularly, the invention relates to heterocyclic benzoate compositions and the stabilization of ultraviolet degradable organic compositions against deterioration resulting from the exposure to such radiations with heterocyclic benzoate compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb electromagnetic radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing heterocyclic benzoate compositions which are resistant to ultraviolet degradation.

It is a still further object of this invention to provide processes for improving the resistance of organic materials to deterioration and degradation by actinic radiation and especially ultraviolet radiation.

It is still further object of this invention to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, organic compositions are provided which are useful as ultraviolet stabilizers or ultraviolet screening agents. These organic compositions consist of heterocyclicsubstituted phenyl group containing compositions connected through a carboxyl group to an aromatic ring which, upon exposure to ultraviolet light, may undergo the "photo-Fries" rearrangement. The organic compositions of the present invention are aryl esters of heterocyclic aromatic acids. The organic compositions of the present invention have the following structure:

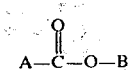

wherein A is a group having the structure

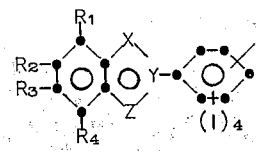

wherein
X and Y are a carbon atom or a nitrogen atom;

Z is an oxygen atom, a sulfur atom, a nitrogen atom, or a nitrogen atom containing a hydrogen atom or a substituted or unsubstituted lower alkyl group containing 1 to 12 carbon atoms;

$R_1$, $R_2$, $R_3$ and $R_4$ are hydrogen, lower alkyl, substituted lower alkyl, cycloalkyl, substituted cycloalkyl, aryl, substituted aryl, lower alkylaryl, aryl-substituted-aryl, chloro, bromo, alkoxy, substituted amino, cyano, and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the Y substituent and the carbon atom attached to the carboxyl group connecting the heterocyclic aromatic A group with the aromatic B group. The carbonyl connecting group is attached to the benzenoid ring in either the meta or para position from the carbon atom connected to the Y substituent. The I substituents can all be one of the substituents listed above or different listed substituents.

The group B is an aryl group of a phenolic aryl component having the formula

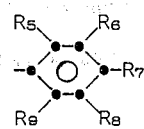

wherein
$R_5$, $R_6$, $R_7$, $R_8$ and $R_9$ are hydrogen, lower alkyl, substituted lower alkyl, cycloalkyl, substituted cycloalkyl, aryl, substituted aryl, lower alkylaryl, aryl-substituted-aryl, alkoxy, hydroxy, substituted amino, carboalkoxy, nitrile, chloro, bromo and the substituents $R_5$ and $R_6$, $R_6$ and $R_7$, $R_7$ and $R_8$, and $R_8$ and $R_9$ combined with the carbon atoms to which they are attached are joined alkylene groups completing a carbocyclic ring which can also be substituted with any of the substituents listed above for $R_5$, $R_6$, $R_7$, $R_8$ and $R_9$. It is necessary that at least one of $R_5$ or $R_9$ be hydrogen so that, on exposure to ultraviolet light, the aryl ester of the heterocyclic aromatic acid is capable by the "photo-Fries" rearrangement of forming a phenol group in that position formerly joined through an oxygen atom to the carbonyl linking group, as for example

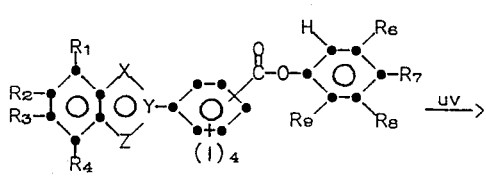

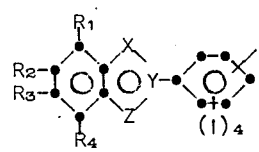

The remaining $R_5$, $R_6$, $R_7$, $R_8$ and $R_9$ can all be one of the substituents listed above or different listed substituents.

Suitable heterocyclic A groups having the structure

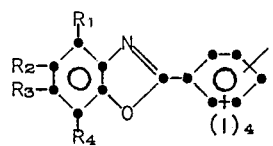

are, for example substituted and unsubstituted benzoxazoles, benzotriazoles, benzothiazoles and benzimidazoles.

Examples of suitable benzoxazole moieties are those having the formula

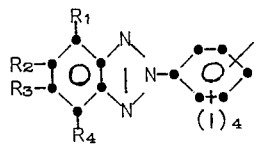

such as 4-(5,6-dimethyl-2-benzoxazolyl)phenyl, 4-(2-benzoxazolyl)-2-chlorophenyl, 3-(5-chloro-2-benzoxazolyl)phenyl.

Examples of suitable benzotriazole moieties are those having the formula

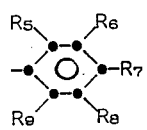

such as 4-(5-chloro-2H-benzotriazol-2-yl)phenyl, 4-(2H-benzotriazol-2-yl)phenyl, 4-(5-methoxy-2H-benzotriazol-2-yl)phenyl.

Examples of suitable benzothiazole moieties are those having the formula

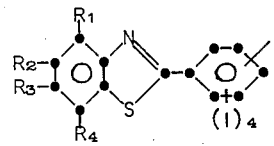

such as 4-(5,6-dimethyl-2-benzothiazolyl)phenyl, 4-(2-benzothiazolyl)-2-chlorophenyl, 3-(5-chloro-2-benzothiazolyl)phenyl.

Examples of suitable benzimidazole moieties are those having the formula

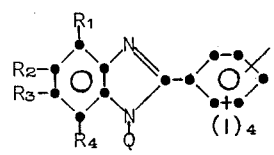

wherein Q is hydrogen or a substituted or unsubstituted lower alkyl group containing 1 to 12 carbon atoms. Such benzimidazole moieties are, for example, 4-(5,6-dimethyl-2-benzimidazolyl)phenyl, 4-(2-benzimidazolyl)-2-chlorophenyl, 3-(5-chloro-2-benzimidazolyl)phenyl, 4-(1-methyl-2-benzimidazolyl)phenyl, 4-(1-ethyl-5-chloro-2-benzimidazolyl)phenyl.

Examples of suitable indole moieties are those having the formula

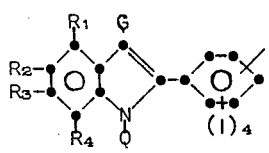

wherein G is the same as $R_1$ and Q is hydrogen or a substituted or unsubstituted lower alkyl group containing 1 to 12 carbon atoms. Such suitable indole moieties are, for example, 3-(1-ethyl-3-cyano-2-indolyl)phenyl, 3-(5-chloro-2-indolyl)phenyl, 3-(1-methyl-2-indolyl)-phenyl, 3-(3-methyl-2-indolyl)phenyl, 3-(3-chloro-2-indolyl)phenyl, 3-(5-acetamido-2-indolyl)phenyl, 3-(2-indolyl)phenyl, 4-(1-ethyl-2-indolyl)phenyl, 4-(3-cyano-2-indolyl)phenyl, 4-(5-methoxy-2-indolyl)-phenyl, 4-(1-methyl-2-indolyl)phenyl, 4-(3-methyl-5-phenyl-2-indolyl)-phenyl, 4-(3,5-dichloro-2-indolyl)phenyl, 4-(2-indolyl)phenyl.

Suitable B groups having the formula are, for example, 2,4-dimethoxyphenyl, 3-methoxyphenyl, 3-methylphenyl, 4-octylphenyl, 4-dodecylphenyl, 3-octylphenyl, 2,4-dichlorophenyl, 4-methoxyphenyl, 2,4-di-t-butylphenyl, 3-(2-ethylhexyloxy)phenyl, 3-dodecyloxyphenyl, 4-cyanophenyl, 4-bromophenyl, 3-hydroxyphenyl and 3-cyclohexylphenol.

"Lower alkyl" as used in this application means branched or unbranched, substituted or unsubstituted alkyl groups containing 1 to 12 carbon atoms. The substituents on the lower alkyl groups can be any of those listed hereinabove for I. "Alkyl" as used herein means branched or unbranched, substituted or unsubstituted alkyl groups containing 1 to 20 carbon atoms which are substituted with the same substituents as $R_1$. Substituted aryl and cycloalkyl groups are also substituted by the same substituents as $R_1$. The "alk" of alkoxy and carboalkoxy means an alkyl radical containing 1 to 20 carbon atoms.

The aryl esters of heterocyclic aromatic acids can be prepared by reacting the acid chloride with a phenol. For example, one group of organic compounds useful as ultraviolet stabilizers is, for example, benzoxazole ester-based compositions having the formula

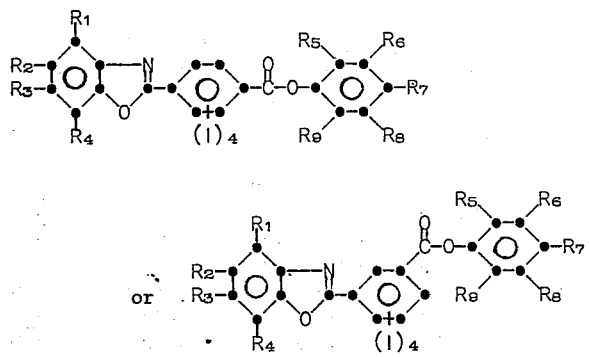

One method for preparing these benzoxazole compounds is illustrated by the following procedure:

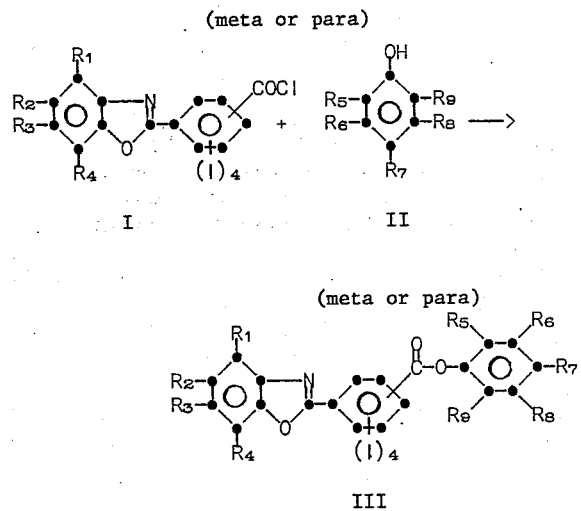

Substituents $R_1$ through $R_9$ and I are defined hereinabove. It is necessary that at least one of $R_5$ and $R_9$ be hydrogen so that, on exposure to ultraviolet light, the aryl ester of the heterocyclic aromatic acid is capable by the "photo-Fries" rearrangement of forming a phenol group in that position formerly joined through an oxygen atom to the carbonyl linking group, as for example

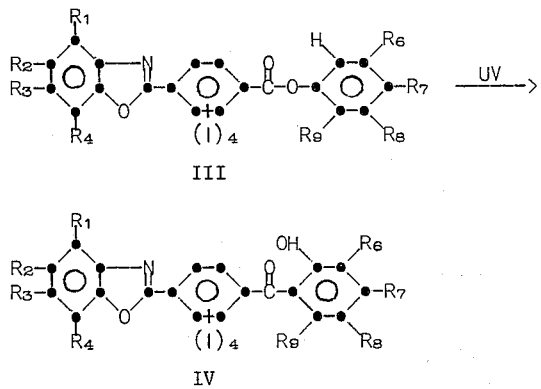

The acid chlorides (I) were prepared by reaction of the corresponding acid [See Zh. Obshch. Khim., 38, 100 1–5 (1968); Chem. Abstr. 69 96568 (1968)] with freshly distilled thionyl chloride [See J. Chem. Soc. 101, 2476 (1912)]. The phenols were obtained from commercial sources, or were prepared by standard methods; a crital requirement is that one of the positions adjacent the phenolic hydroxyl group be unsubstituted.

The heterocyclic phenyl benzoate compositions can be added to organic compositions which are susceptible to ultraviolet degradation. Such compositions include, for example, polymeric compositions such as polyester fiber and moldable compositions, such as poly(ethylene terephthalate), poly(tetramethylene terephthalate), unsaturated polyester resins and the like; polyolefins such as, for example, high, medium and low density polyethylene, polypropylene, polybutene and the like; polyamides such as N-methoxymethyl polyhexamethylene adipamide and the like; polycarbonates; polyvinyl chloride and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene/vinyl acetate copolymers; cellulose ethers such as methyl cellulose; polyvinyl esters such as polyvinyl acetate; polyethylene oxides; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The heterocyclic phenyl benzoate compositions as effective ultraviolet stabilizers or screening agents are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions containing the stabilizers of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These heterocyclic phenyl benzoate ultraviolet stabilizers may be incorporated into organic compositions by melt-blending or may be added onto the surface of an organic plastic material prior to being molded into a suitable object, or added to the surface of the molded object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

4-(1,1,3,3-Tetramethylbutyl)phenyl 4-(2-benzoxazolyl)benzoate can be prepared by the following procedure:

To a solution of 4.0 g. (0.1 mole) of sodium hydroxide in 200 ml. of water was added 20.6 g. (0.1 mole) of 4-(1,1,3,3-tetramethylbutyl)phenol. The mixture was stirred for 10 minutes and 200 ml. of chloroform was added, followed by the dropwise addition of a solution of 25.7 g. (0.1 mole) of 4-(2-benzoxazolyl)benzoyl chloride in 500 ml. of chloroform. The mixture was stirred at reflux for 3 hours after the addition was completed. The reaction mixture was cooled to 30°C. and the chloroform layer separated and washed with water until neutral. The solvent was concentrated to about one-half the original volume, chilled and the crude product collected by filtration. The off-white solid was recrystallized from toluene to give 32 g. (81%) of white plates, m.p. 209°–210°C.

Other phenyl benzoxazolylbenzoate esters can be prepared by substituting other benzoxazolylbenzoyl chlorides, such as 4-(5,6-dimethyl-2-benzoxazolyl)-benzoyl chloride, 4-(2-benzoxazolyl)-2-chloro-benzoyl chloride, 3-(5-chloro-2-benzoxazolyl)benzoyl chloride, 4-(5,6-dichloro-2-benzoxazolyl)benzoyl chloride, 4-(5,6-diethyl-2-benzoxazolyl)benzoyl chloride, 4-(5-cyano-2-benzoxazolyl)benzoyl chloride, 4-(5-methoxy-6-methyl-2-benzoxazolyl)benzoyl chloride, for 4-(2-benzoxazolyl)benzoyl chloride.

Also, other phenyl benzoxazolylbenzoate esters can be prepared by substituting other phenols, such as 2,4-dimethoxyphenol, 3-methoxyphenol, 3-methylphenol, 4-octylphenol, 4-dodecylphenol, 3-octylphenyl, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for 4-(1,1,3,3-tetramethylbutyl)phenol.

EXAMPLE 2

3-Methylphenyl 4-(2-benzoxazolyl)benzoate can be similarly prepared by the procedure of Example 1 as follows:

10.8 g. m-cresol (0.1 mole) was added to a solution of 4.0 g. (0.1 mole) sodium hydroxide in 200 ml. of water. A solution of 25.7 g. (0.1 mole) of 4-(2-benzoxazolyl)benzoyl chloride was added and refluxing continued for 3 hours. On workup, 26 g. (79%) of a white solid (plates) was obtained; m.p. 160°–161°C.

EXAMPLE 3

3-Methoxyphenyl 4-(2-benzoxazolyl)benzoate can be similarly prepared by the procedure of Example 1 as follows:

12.4 g. (0.1 mole) of m-methoxyphenol was added to a solution of 4.0 g. (0.1 mole) NaOH in 200 ml. of water. A solution of 25.7 g. (0.1 mole) of 4-(2-benzoxazolyl)benzoyl chloride in 400 ml. of chloroform was added and refluxing continued for 2 hours. On workup, 28 g. of a white solid was obtained, m.p. 138°–139°C.

EXAMPLE 4

3-Methylphenyl 4-(2-benzotriazolyl)benzoate can be similarly prepared by the procedure of Example 1 as follows:

10.8 g. m-cresol (0.1 mole) was added to a solution of 4.0 g. (0.1 mole) sodium hydroxide in 200 ml. of water. A solution of 25.8 g. (0.1 mole) of 4-(2-benzotriazolyl)benzoyl chloride was added and refluxing continued for 3 hours after the addition was completed. The reaction mixture was cooled to 30°C. and the chloroform layer separated and washed with water until neutral. The solvent was concentrated to about onehalf the original volume, chilled and the crude product collected by filtration.

Other phenyl benzotriazolylbenzoates can be prepared by substituting other benzotriazolylbenzoyl chlorides, such as 4-(5,6-dimethyl-2-benzotriazolyl)benzoyl chloride, 4-(2-benzotriazolyl)-2-chlorobenzoyl chloride, 3-(5-chloro-2-benzotriazolyl)benzoyl chloride, 4-(5,6-dichloro-2-benzotriazolyl)benzoyl chloride, 4-(5,6-diethyl-2-benzotriazolyl)benzoyl chloride, 4-(5-cyano-2-benzotriazolyl)benzoyl chloride, 4-(5-methoxy-6-methyl-2-benzotriazolyl)benzoyl chloride, for 4-(2-benzotriazolyl)benzoyl chloride.

Also, other phenyl benzotriazolylbenzoate esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4di-t-butylphenol, for m-cresol.

EXAMPLE 5

3-Methylphenyl 4-(2-benzothiazolyl)benzoate can be similarly prepared by the procedure of Example 1 as follows:

10.8 g. m-cresol (0.1 mole) was added to a solution of 4.0 g. (0.1 mole) sodium hydroxide in 200 ml. of water. A solution of 27.4 g. (0.1 mole) of 4-(2-benzothiazolyl)benzoyl chloride was added and refluxing continued for 3 hours after the addition was completed. The reaction mixture was cooled to 30°C. and the chloroform layer separated and washed with water until neutral. The solvent was concentrated to about onehalf the original volume, chilled and the crude product collected by filtration.

Other phenyl benzothiazolylbenzoates can be prepared by substituting other benzothiazolylbenzoyl chlorides, such as 4-(5,6-dimethyl-2-benzothiazolyl)benzoyl chloride, 4-(2-benzothiazolyl)-2-chlorobenzoyl chloride, 3-(5-chloro-2-benzothiazolyl)benzoyl chloride, 4-(5,6-dichloro-2-benzothiazolyl)benzoyl chloride, 4-(5,6-diethyl-2-benzothiazolyl)benzoyl chloride, 4-(5-cyano-2-benzothiazolyl)benzoyl chloride, 4-(5-methoxy-6-methyl-2-benzothiazolyl)benzoyl chloride, for 4-(2-benzothiazolyl)benzoyl chloride.

Also, other phenyl benzothiazolylbenzoate esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for m-cresol.

EXAMPLE 6

3-Methylphenyl 4-(2-benzimidazolyl)benzoate can be similarly prepared by the procedure of Example 1 as follows:

10.8 g. m-cresol (0.1 mole) was added to a solution of 4.0 g. (0.1 mole) sodium hydroxide in 200 ml. of water. A solution of 25.7 g. (0.1 mole) of 4-(2-benzimidazolyl)benzoyl chloride was added and refluxing continued for 3 hours after the addition was completed. The reaction mixture was cooled to 30°C. and the chloroform layer separated and washed with water until neutral. The solvent was concentrated to about onehalf the original volume, chilled and the crude product collected by filtration.

Other phenyl benzimidazolylbenzoates can be prepared by substituting other benzimidazolylbenzoyl chlorides, such as 4-(5,6-dimethyl-2-benzimidazolyl)benzoyl chloride, 4-(2-benzimidazolyl)-2-chlorobenzoyl chloride, 3-(5-chloro-2-benzimidazolyl)benzoyl chloride, 4-(5,6-dichloro-2-benzimidazolyl)benzoyl chloride, 4-(5,6-diethyl-2-benzimidazolyl)benzoyl chloride, 4-(5-cyano-2-benzimidazolyl)benzoyl chloride, 4-(5-methoxy-6-methyl-2-benzimidazolyl)benzoyl chloride, for 4-(2-benzimidazolyl)benzoyl chloride.

Also, other phenyl benzimidazolylbenzoate esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for m-cresol.

EXAMPLE 7

3-Methylphenyl 4-(2-indolyl)benzoate can be similarly prepared by the procedure of Example 1 as follows:

10.8 g. m-cresol (0.1 mole) was added to a solution of 4.0 g. (0.1 mole) sodium hydroxide in 200 ml. of water. A solution of 25.6 g. (0.1 mole) of 4-(2-indolyl)benzoyl chloride was added and refluxing continued for 3 hours after the addition was completed. The reaction mixture was cooled to 30°C. and the chloroform layer separated and washed with water until neutral. The solvent was concentrated to about one-half the original volume, chilled and the crude product collected by filtration.

Other phenyl indolylbenzoates can be prepared by substituting other 2-indolybenzoyl chlorides, such as 4-(5,6-dimethyl-2-indolyl)benzoyl chloride, 4-(2-indolyl)-2-chlorobenzoyl chloride, 3-(5-chloro-2-indolyl)benzoyl chloride, 4-(5,6-dichloro-2-indolyl)benzoyl chloride, 4-(5,6-diethyl-2-indolyl)benzoyl chloride, 4-(5-cyano-2-indolyl)benzoyl chloride, 4-(5-methoxy-6-methyl-2-indolyl)benzoyl chloride, for 4-(2-indolyl)benzoyl chloride.

Also, other phenyl 2-indolylbenzoate esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 4-methoxyphenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 2,4-di-t-butylphenol, for m-cresol.

EXAMPLE 8

The ultraviolet stabilization provided by the heterocyclic phenyl benzoates of the present invention is shown in poly(tetramethylene terephthalate) in Tables 1 and 3 and polypropylene in Table 2.

Table 1

Weathering Data for Stabilizers in Poly(tetramethylene terephthalate) in Atlas XWR-1 Weather-Ometer

| Stabilizer (1% Concentration) | Initial FWIS* | FWIS- 3000 hr. Exposure |
|---|---|---|
| Control (no stabilizer) | 17 | 1 |
| 4-(1',1,3,3-Tetramethylbutyl)phenyl 4-(2-benzoxazolyl) benzoate | 17 | 17 |
| 3-Methoxyphenyl 4-(2-benzoxazolyl) benzoate | 18 | 19 |

*FWIS is Flatwise Impact Strength.

Table 2

Typical Weathering Data for Stabilizers in 5-Mil Polypropylene Film Exposed in FL-WOM Weather-Ometer

| Stabilizer (1% Concentration) | Time to Embrittlement (Hours) |
|---|---|
| 4-(1,1,3,3-Tetramethylbutyl)phenyl 4-(2-benzoxazolyl) benzoate | 627 |
| Control (no stabilizer) | 175 |

Table 3

Typical Weathering Data for Stabilizers in 1/16" Poly(tetramethylene terephthalate) Flat Bars Weathered by a 1000-w Mercury Lamp

| Stabilizer (%)[a] | FWIS[b] 0 | 300 | 500 |
|---|---|---|---|
| 3-Methoxyphenyl 3-(2-benzoxazolyl)benzoate | 18 | 18 | 14 |
| 4-Cyanophenyl 4-(2-benzoxazolyl)benzoate | 17 | 17 | 13 |

Table 3-continued

Typical Weathering Data for Stabilizers in 1/16" Poly(tetramethylene terephthalate) Flat Bars Weathered by a 1000-w Mercury Lamp

| Stabilizer (%)[a] | 0 | FWIS[b] 300 | 500 |
|---|---|---|---|
| 3,4-Di-t-butylphenyl 4-(5,6-dimethyl-2-benzoxazolyl)benzoate | 18 | 17 | 17 |
| 3-Methylphenyl 4-(5-chloro-2-benzoxazolyl)benzoate | 19 | 17 | 16 |
| 2,4-Dichlorophenyl 3-(2-benzothiazolyl)benzoate | 19 | 16 | 12 |
| 3-Bromophenyl 3-(5-chloro-2-benzothiazolyl)benzoate | 18 | 17 | 12 |
| 3-n-Butoxyphenyl 4-(2-benzothiazolyl)benzoate | 19 | 19 | 19 |
| 3-Cyclohexylphenyl 4-(6-methyl-2-benzothiazolyl)benzoate | 17 | 16 | 16 |
| 4-Phenylphenyl 3-(1-methyl-2-benzimidazolyl)benzoate | 19 | 14 | 12 |
| 3-Dodecyloxyphenyl 4-(2-benzimidazolyl)benzoate | 19 | 19 | 19 |
| 3,5-Dimethylphenyl 4-(5-chloro-2-benzimidazolyl)benzoate | 19 | 19 | 18 |
| 3-Methoxyphenyl 4-(2-benzimidazolyl)benzoate | 18 | 18 | 18 |
| 3-Ethoxyphenyl 4-(2-benzotriazolyl)benzoate | 19 | 18 | 18 |
| 3-Phenylphenyl 4-(2-benzotriazolyl)benzoate | 17 | 16 | 16 |
| 4-Cyanophenyl 4-(5-chloro-2-benzotriazolyl)benzoate | 19 | 14 | 12 |
| 3-Dodecyloxyphenyl 4-(5-bromo-2-benzotriazolyl)benzoate | 18 | 18 | 18 |
| 3-Phenoxyphenyl 3-(3-chloro-2-indolyl)benzoate | 18 | 18 | 18 |
| 4-Bromophenyl 3-(2-indolyl)benzoate | 19 | 16 | 12 |
| 2,4-Dimethylphenyl 4-(3,5-dichloro-2-indolyl)benzoate | 19 | 14 | 12 |
| 3-chlorophenyl 4-(2-indolyl)benzoate | 19 | 14 | 13 |
| None | 19 | 5 | 1 |

[a]Incorporated into the polyester (1.50 I.V.) by dry-blending the powdered components, extrusion into 1/16" dia. rod and injection molding into 1/16" thick flat bars.
[b]Flatwise-Impact-Strength (ft.-lb./in.²) after exposure to mercury lamps for the hours indicated.

These aryl esters of heterocyclic aromatic acid compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials, and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. A compound of the formula:

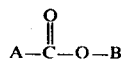

wherein A is a group having the structure

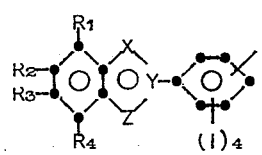

wherein
X is a nitrogen atom, Y is a carbon atom; and
Z is an oxygen atom;
$R_1$, $R_2$, $R_3$ and $R_4$ are hydrogen, chloro, bromo, lower alkyl,
I is the same as $R_1$, $R_2$, $R_3$ and $R_4$ and is present on all positions of the benzenoid ring, except the carbon atom attached to the Y substituent and the carbon atom attached to the carboxyl group connecting the heterocyclic aromatic A group with the aromatic B group, said carbonyl connecting group is attached to the benzenoid ring in either the meta or para position from the carbon atom connected to the Y substituent; and B is a group having the formula

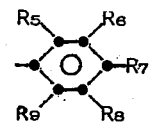

wherein
at least one $R_5$ or $R_9$ is hydrogen and the other $R_5$, $R_6$, $R_7$, $R_8$ and $R_9$ are hydrogen, lower alkyl, hydroxy, nitrile, chloro or bromo.

2. A compound according to claim 1 having the formula:

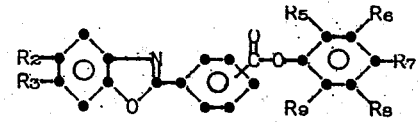

wherein $R_2$ is hydrogen, lower alkyl, or nitrile; $R_3$ is hydrogen or lower alkyl; and $R_5$, $R_6$, $R_7$, $R_8$ and $R_9$ are hydrogen, lower alkyl, halogen, or nitrile,.

3. A compound according to claim 2 having the formula:

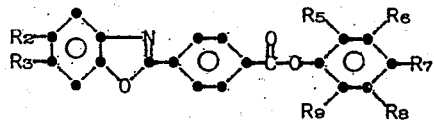

wherein $R_2$ is hydrogen, lower alkyl, or nitrile; $R_3$ is hydrogen or lower alkyl; and $R_5$, $R_6$, $R_7$, $R_8$ and $R_9$ are hydrogen, lower alkyl, halogen, or nitrile.

4. A compound according to claim 2 having the formula:

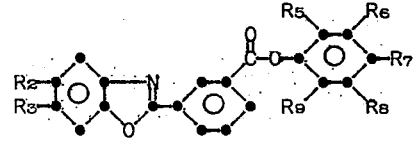

wherein $R_2$ is hydrogen, lower alkyl, or nitrile; $R_3$ is hydrogen or lower alkyl; and $R_5$, $R_6$, $R_7$, $R_8$ and $R_9$ are hydrogen, lower alkyl, halogen, or nitrile.

5. A compound according to claim 3 wherein said stabilizing compound has the formula:

wherein $R_2$ is hydrogen, lower alkyl, or nitrile; $R_3$ is hydrogen or lower alkyl; and $R_6$ is lower alkyl.

6. A compound according to claim 5 having the formula:

wherein $R_2$ and $R_3$ are hydrogen or lower alkyl and $R_6$ is lower alkyl.

7. A compound according to claim 6 having the formula

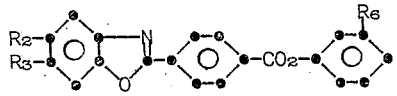

wherein $R_2$ and $R_3$ are hydrogen or lower alkyl and $R_6$ is lower alkyl containing 1 to 12 carbon atoms.

8. A compound having the formula:

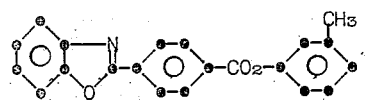

9. A compound having the formula:

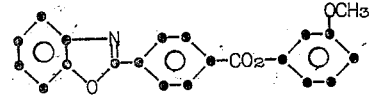

10. A compound having the formula:

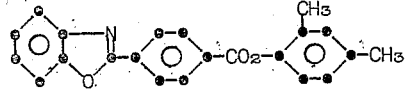

11. A compound having the formula:

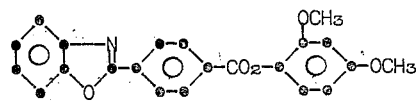

12. A compound having the formula:

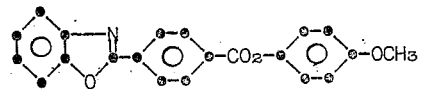

13. A compound having the formula:

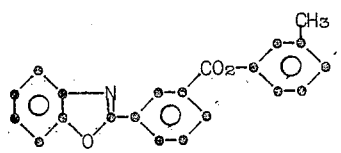

14. A compound having the formula:

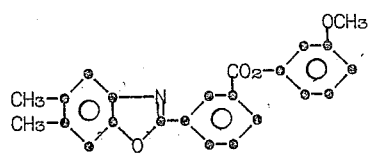

15. A compound having the formula:

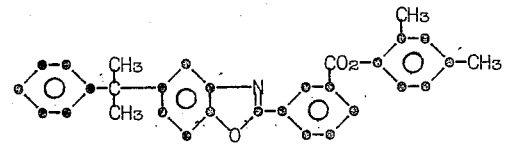

16. A compound having the formula:

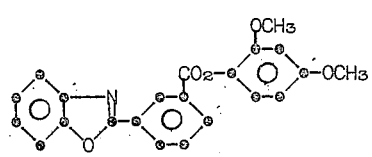

* * * * *

UNITED STATES PATENT OFFICE
CERTIFICATE OF CORRECTION

Patent No. 3,957,813                Dated May 18, 1976

Inventor(s) Gether Irick, Jr. and Charles A. Kelly

It is certified that error appears in the above-identified patent and that said Letters Patent are hereby corrected as shown below:

In the Heading, the line at [22] should read

---Filed: July 1, 1974---  .

Column 11, line 63, after "alkyl," add ---and cyano;---.

Signed and Sealed this

Twenty-fourth Day of August 1976

[SEAL]

Attest:

RUTH C. MASON  
*Attesting Officer*

C. MARSHALL DANN  
*Commissioner of Patents and Trademarks*